United States Patent [19]

Sweeney

[11] Patent Number: Plant 7,626

[45] Date of Patent: Aug. 20, 1991

[54] *LANTANA SELLOWIANA* CV. MONSWEE

[76] Inventor: Anna M. Sweeney, c/o Botanical Dept., Monrovia Nursery Company, P.O. Box Q, Azusa, Calif. 91702

[21] Appl. No.: 485,327

[22] Filed: Feb. 23, 1990

[51] Int. Cl.[5] ..... A01H 5/00

[52] U.S. Cl. ..... Plt./68

[58] Field of Search ..... Plt./54

[56] References Cited

PUBLICATIONS

Bailey, L. H., "Lantana" *The Standard Cyclopedia of Horticulture,* vol. II, 1935 The Macmillan Company, N.Y., pp. 1818–1820.

*Primary Examiner*—James R. Feyrer

[57] ABSTRACT

A new and distinct selection of Lantana groundcover which shall be referred to hereinafter as *Lantana sellowiana* cultivar Monswee, also known as *Lantana montevidensis* cultivar Monswee. *Lantana sellowiana* cultivar Monswee differs distinctively from other *Lantana sellowiana* plants by its unique combination of whitish flower heads interspersed with the typical purplish flower heads.

1 Drawing Sheet

BACKGROUND OF THE INVENTION

This invention relates to a new and distinct selection of *Lantana sellowiana,* a member of the Verbenaceae or Verbena Family. *Lantana sellowiana* cultivar Monswee was discovered in a group of my *Lantana sellowiana* selection that were under evaluation at Monrovia Nursery Company, 18331 E. Foothill Boulevard, Azusa, Calif. in the early spring of 1989.

My new selection has been strictly asexually reproduced by cuttings at Monrovia Nursery Company. The distinct phenotypic characteristic of this new selection that sets this plant apart from other *Lantana sellowiana* plants could be lost genetically through sexual reproduction. Therefore, sexual reproduction is prohibited and propagation is restricted to asexual reproduction by cuttings. Seed progency from the new selection has not been observed.

SUMMARY OF THE INVENTION

*Lantana sellowiana* cv. Monswee is unique. This species is *not* to be confused with *Lantana camara* or its hybrids which are bush forms and have flower colors of variations of yellow, orange or red. The typical widely planted *Lantana sellowiana* blooms only with purplish flowers. A white flowered selection has recently become available. However, to my knowledge, a selection with purplish and whitish flowers on the same plant has not been in existence prior to my selection. This characteristic of purplish and whitish flowers on the same plant is the most obvious difference and does set my selection apart from other *Lantana sellowiana* plants.

BRIEF DESCRIPTION OF THE DRAWING

The accompanying illustration shows a typical specimen of the plant according to this invention and is depicted in color as nearly true as possible. The illustration depicts a close up on my new selection and displays the whitish flower heads mixed with the typical purplish flower heads.

BOTANICAL DESCRIPTION OF THE CLAIMED PLANT

Below is a detailed description of the new *Lantana sellowiana* cv. Monswee, the color terminology is from the British Horticultural Color Charts.

Overall size and habit and vigor: Dense mounding growth habit with trailing stems. After 5 years plant should achieve a height of 12–15" with a spread of 6–8'. With age spreading branches will root. This selection is a vigorous rapid grower similar in vigor to the species.

Tolerance to cold temperatures: Plant is evergreen to approximately 20 F. temperatures. Plant will survive winters down to 0 F. in the Tucson area, however, at this temperature-top growth is completely killed back, roots will survive and new shoots will resprout from the ground each spring.

Tolerance to high temperatures: *Lantana sellowiana* is widely used in areas of high heat 100 F.–115 F. as the plant will survive and thrive in high temperatures. This tolerance exists for the new selection also.

Tolerance to drought: The species *Lantana sellowiana* is a highly recommended water wise/drought tolerant ground cover. My new selection to date has shown the same drought tolerant attributes.

Flower: Free flowering throughout the year in Southern California.

*Arrangement.*—Flowers complete, small, sessile in axils of the bracts, in long peduncled dense heads arising from leaf axils. Peduncle length ranging from 2.0 cm to 4.0 cm. Flower clusters are normally above foliage. Flower counts per cluster do not appear to vary with age or season.

*Color.*—The unique characteristic. Flower clusters in heads are either a whitish or purplish, occasionally some of the purplish flowers will exhibit a white eye. Color variation is not observed to change with the age of flowers or change with seasonal temperatures or light intensity. It is believed this plant is a chimera which results in the separate flower head colors. White: Appearance is white though the color is Pastel Mauve 433/3. Occasionally an edge or splotch of Imperial Purple 33/2 exists on a few flowers. Purple: Flower color is Imperial Purple 33/1 with slight fading to Imperial Purple 33/2. Most all the flowers are a solid color though 30–40 percent exhibit a central eye of Pastel Mauve.

*Size.*—White flower length: 0.8–1.0 cm. White flower width: 0.6–0.8 cm. Purple flower length: 1.0–1.1 cm. Purple flower width: 0.7–0.9 cm. White flowers tend to be slightly smaller.

*Shape.*—Corolla somewhat irregularly 4–5 parted, corolla tube slender.

Leaf:

*Arrangement.*—Opposite.

*Size.*—Length varies 3.0 cm–2.0 cm. Width varies 1.8 cm–1.0 cm. Leaf measurement made on older plants, not on young rapidly growing branches.

*Fragrance.*—Strong pungent smell particularly when crushed.

*Texture.*—Slightly coriaceus with deep reticulated veination.

*Color.*—Lower surface: Spinach Green 0960/3. Upper surface: Ivy Green 0001060/3.

*Shape.*—Narrow — deltoid to ovate.

*Margins.*—Crenate.

*Pubescense.*—Puberulent on upper and lower leaf surface.

Fruit: Not observed, likely a cluster of small dark dupes.

I claim:

1. A new and distinct selection of Lantana as substantially shown and described herein, that is characterized particularly as a novelty by the unique combination of whitish flower heads interspersed with the typical purplish flower heads.

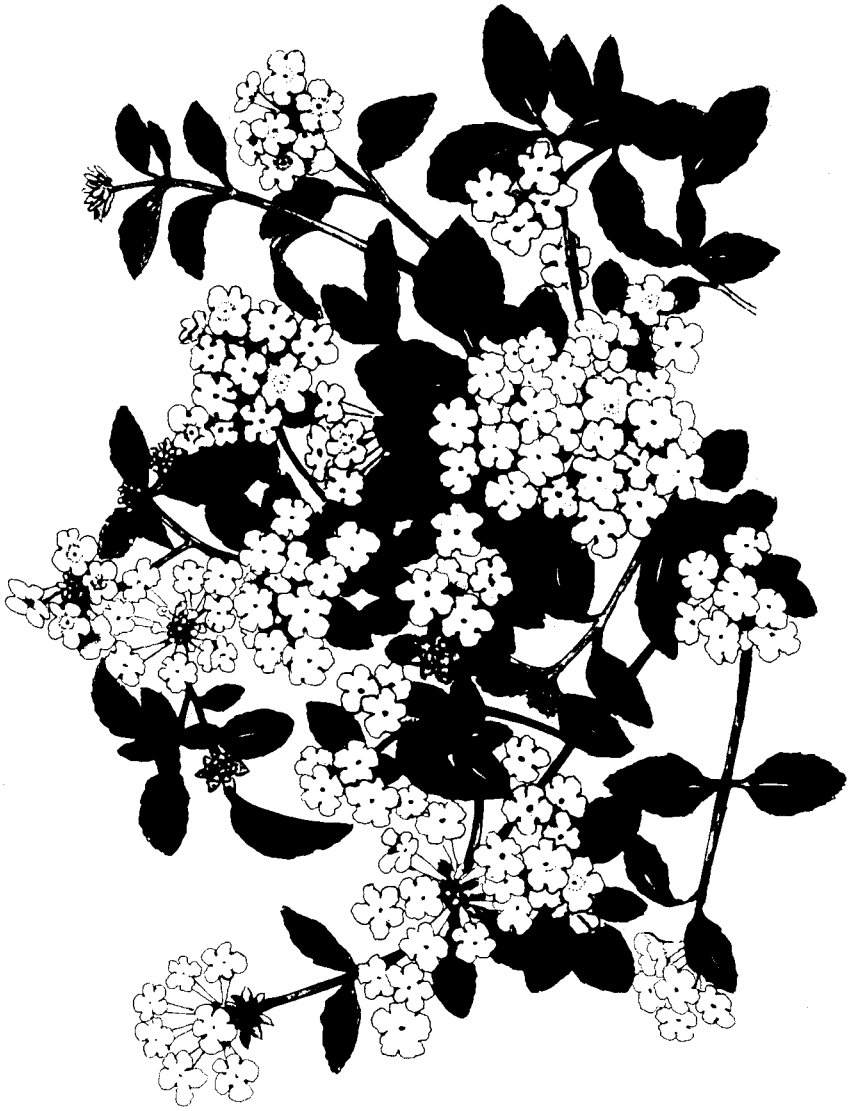

* * * * *